United States Patent [19]
Schwartz

[11] Patent Number: 5,391,177
[45] Date of Patent: Feb. 21, 1995

[54] OPHTHALMIC LANCE

[76] Inventor: Daniel M. Schwartz, 44 Calhoun Ter., San Francisco, Calif. 94133

[21] Appl. No.: 17,508

[22] Filed: Feb. 12, 1993

[51] Int. Cl.⁶ .......................................... A61B 17/32
[52] U.S. Cl. .................... 606/167; 606/166; 30/162; 30/151
[58] Field of Search .............. 606/166, 167, 170, 172, 606/181; 30/151, 162, 286, 293, 335

[56] References Cited

U.S. PATENT DOCUMENTS

| | | | |
|---|---|---|---|
| 845,792 | 3/1907 | Jenkins | 30/162 |
| 1,208,608 | 12/1916 | Meadwell | 30/162 |
| 1,360,490 | 11/1920 | Bahde | 30/162 |
| 1,611,171 | 12/1926 | Easton | 30/162 |
| 3,657,812 | 4/1972 | Lee | 30/162 |
| 3,756,242 | 9/1973 | Coss | 606/167 |
| 3,885,308 | 5/1975 | Gordin | 30/162 |
| 4,499,898 | 2/1985 | Knepshield et al. | 606/170 |
| 4,576,164 | 3/1986 | Richeson | 30/162 |
| 4,674,500 | 6/1987 | DeSatnick | 606/170 |
| 5,275,606 | 1/1994 | Abidin et al. | 606/167 |
| 5,309,641 | 5/1994 | Wonderley et al. | 606/167 |
| 5,330,492 | 7/1994 | Haugen | 606/167 |
| 5,330,493 | 7/1994 | Haining | 606/167 |

FOREIGN PATENT DOCUMENTS

| | | | |
|---|---|---|---|
| 671872 | 10/1989 | Switzerland | 606/167 |
| 2113550 | 8/1983 | United Kingdom | 606/166 |
| 1367970 | 1/1988 | U.S.S.R. | 606/166 |

Primary Examiner—Ralph A. Lewis
Attorney, Agent, or Firm—Haverstock, Medlen & Carroll

[57] ABSTRACT

An ophthalmic lance includes a retractable blade and a sheath, the retractable blade can only be exposed when a button is pressed down. The blade is attached to a spring loaded stem so that when the button is released, the blade is automatically retracted back into the sheath. Pressure on the button at the end of the stem or on the locking pin causes the blade to be exposed. As soon as that pressure is released the blade is automatically retracted back up into the sheath. The sheath has an H-shaped cutout in which a locking pin fits in and can slide about. The locking pin is coupled to the stem. The H-shaped cutout has a short-leg, a long-leg and a cross-bar so that when the locking pin is inside of the short-leg, the blade is in the locked position and when the locking pin is inside of the long-leg, the stem can be depressed and the blade exposed. To switch back and forth between the locked and the unlocked positions the stem must be rotated relative to the sheath so that the locking pin travels between the short-leg and the long-leg through the cross-bar of the H-shaped cutout.

10 Claims, 1 Drawing Sheet

OPHTHALMIC LANCE

FIELD OF THE INVENTION

This invention relates to the field of surgical knife instruments. More specifically, this invention relates to the field of sheathed surgical knife instruments.

BACKGROUND OF THE INVENTION

Ophthalmic surgery requires very delicate and precise incisions, frequently performed under a microscope and dealing with microscopic dimensions. The instrumentation used by the surgeon for this type of operation is extremely specialized and must be precisely exact. The sharpness of the instrument used to make the incisions is critical to the success of the operation.

One prior art device, currently in use, is a disposable microvitreoretinal blade which is essentially an open blade attached to a stem. The blade of this device is exposed at all times and there is a significant risk that the surgeon or other operating room personnel may inadvertently be injured by the extremely sharp, exposed blade. Not only might the surgical personnel be cut by the blade, but it is possible that they could be infected by HIV, hepatitis virus or other pathogens. Wearing surgical gloves will not alleviate this problem because the instrument required during the surgery is sharp enough to puncture surgical gloves very easily. For these reasons, it is advantageous that an ophthalmic lance is used which possesses a sheath to cover the blade and protect the user from injury.

In U.S. Pat. No. 4,414,974 Dotson et al. presented a one-time-use microsurgical knife with a slidable shroud that can be moved into a forward, sheathed position to protect the blade, and can be moved back to allow use of the knife. The shroud 18 of Dotson et al.'s invention slides down the cylindrical member 11 to cover the smaller forward tip 14 and the cutting blade 15. To then expose the blade 15, the user must slide the shroud 18 back up the cylindrical member 11.

In U.S. Pat. No. 4,360,016 Sarrine presented a blood collecting device which includes a lancet blade 40 which is exposed and locked in an extended position by pressing the button 48. To retract the lancet blade 40, the finger 50 is pressed causing the lancet blade 40 to retract within the outer surface 17 of the collar 16.

In U.S. Pat. No. 4,491,132 Aikins presented a sheath and retractable surgical tool combination to be used in closed surgical procedures, such as arthroscopy. The protective sheath 10 allows the scalpel blade 30 to be inserted into the actual operative site of the body, minimizing the accidental cutting of surrounding tissue. To then expose the blade 30, the sheath 10 is slid up the blade handle 40 until the pin 26 engages a hole 58 at the desired position. The blade 30 can be exposed at a plurality of positions from partial exposure to full exposure of the blade 30.

In U.S. Pat. No. 4,733,662 DeSatnick et al. presented a tissue gripping and cutting assembly for surgical instruments which includes a reusable handle and a removable sheathed blade assembly. The blade assembly 24 is exposed or retracted by an internal slider 26 controlled by a single finger manipulable external slide button 28.

In U.S. Pat. No. 5,071,426 Dolgin et al. presented a surgical scalpel with retractable blade guard which is mounted for movement between a blade-guarded position and a blade exposed position. Depressing the actuating arm 18 towards the body 12 will cause the blade guard 16 to slide backwards to expose the blade 14. To release the guard and again cover the blade, the surgeon must again apply pressure to the actuating arm 18.

None of these references in the prior art present a surgical instrument with a blade that is automatically retractable and is only exposed while the user is pressing a button. What is needed for the safety of patients, surgeons and medical staff, is a surgical instrument that includes a blade which is automatically retractable and is only exposed while the user is pressing a button, and the surgical instrument also including a locking position which will not allow the blade to be exposed even when the button is pressed.

SUMMARY OF THE INVENTION

An ophthalmic lance includes a retractable blade and a sheath, the retractable blade can only be exposed when a button is pressed down. The blade is attached to a spring loaded stem so that when the button is released, the blade is automatically retracted back into the sheath. Pressure on the button at the end of the stem or on the locking pin causes the blade to be exposed. As soon as that pressure is released the blade is automatically retracted back up into the sheath. The sheath has an H-shaped cutout in which a locking pin fits in and can slide about. The locking pin is coupled to the stem. The H-shaped cutout has a short-leg, a long-leg and a cross-bar so that when the locking pin is inside of the short-leg, the blade is in the locked position and when the locking pin is inside of the long-leg, the stem can be depressed and the blade exposed. To switch back and forth between the locked and the unlocked positions the stem must be rotated relative to the sheath so that the locking pin travels between the short-leg and the long-leg through the cross-bar of the H-shaped cutout.

DETAILED DESCRIPTION OF THE PREFERRED EMBODIMENT

Figure 1:
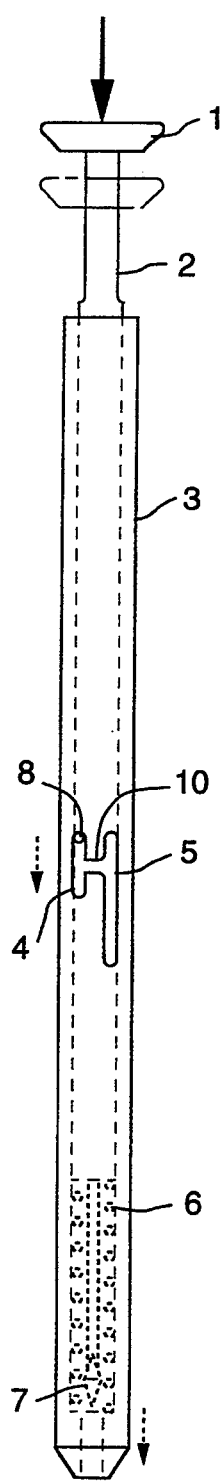
FIG. 1 illustrates the ophthalmic lance in a locked position.

The ophthalmic lance of the present invention is illustrated in FIG. 1. The ophthalmic lance has a sheath 3 which covers a blade 7. The blade 7 is part of a stem 2 that extends through the sheath and the end of the stem 2 opposite from the blade 7 has a button 1. Inside the sheath 3 is a spring 6 which operates between the stem 2 and the bottom of the sheath 3. The spring 6 causes the stem 2 to automatically retract when the button 1 is released. The stem 2 is held in position inside the sheath 3 by a locking pin 8 which is inserted through the sheath 3 and into the receiving hole 9 in the stem 2. The outside of the sheath 3 has an H-shaped cutout which also engages the locking pin 8. The H-shaped cutout has a short-leg 4, a long-leg 5, and a cross-bar 10. The short-leg 4 and the long-leg 5 are connected by the cross-bar 10 of the H-shaped cutout.

Figure 2:
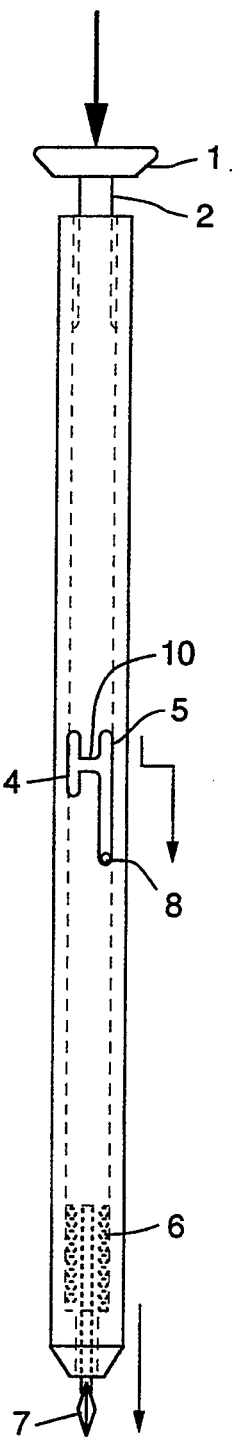
FIG. 2 illustrates the ophthalmic lance in an unlocked position, where pressure on the button causes the blade to be exposed.

The blade 7 of the ophthalmic lance is only exposed when the locking pin 8 is in the long-leg 5 of the H-shaped cutout and the button 1 is depressed as is illustrated in FIG. 2. When the button 1 is released, the spring 6 causes the stem 2 to be pushed upward and the blade 7 is then retracted into the sheath 3. The locking pin 8 will only allow the stem 3 to be pushed down until the locking pin 8 hits the bottom of the long-leg 5 of the H-shaped cutout. The length of the long-leg 5 of the H-shaped cutout can be determined so that the blade is extended to its optimum length for the surgeon using the ophthalmic lance. In the preferred embodiment of the present invention the long-leg 5 of the H-shaped cutout is approximately 12 mm.

When the locking pin 8 is in the short-leg 4 of the H-shaped cutout, as is illustrated in FIG. 1, the stem 2 can only be pushed down until the locking pin 8 hits the bottom of the short-leg 4 of the H-shaped cutout. The length of the short-leg 4 can be determined so that the blade 7 will not be exposed when the stem 2 is pushed down to the point where the locking pin 8 is hitting the bottom of the short-leg 4 of the H-shaped cutout. In the preferred embodiment of the present invention the short-leg 4 of the H-shaped cutout is approximately 7 mm.

Figure 3:
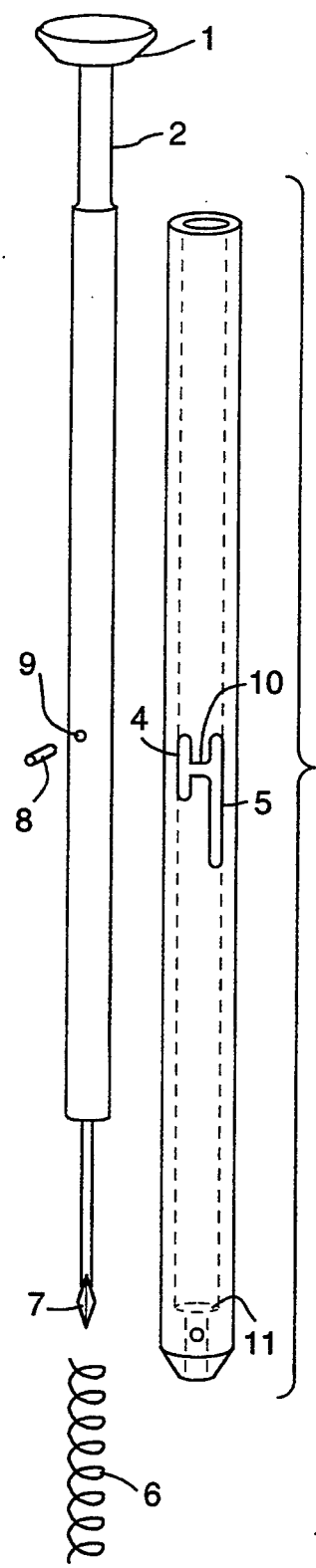
FIG. 3 illustrates the unassembled parts of the ophthalmic lance including the stem, the blade, the spring, the pin, and the sheath.

The individual pieces of the ophthalmic lance are illustrated in FIG. 3 so that assembly of the ophthalmic lance can be explained. To assemble the ophthalmic lance the spring 6 must first be inserted in the sheath 3 from the top until it rests on the neck 11 of the sheath 3 at the point where the diameter of the interior hollow cavity of the sheath 3 is reduced. The stem 2 must then be inserted into the inside of the sheath 3, blade 7 first, from the top and slid down so that the blade 7 extends through the center of the spring 6 and is positioned to extend through the neck 11 of the sheath 3. The stem 2 must then be pulled up until the receiving hole 9 can be seen through the H-shaped cutout and the locking pin 8 can be inserted through the H-shaped cutout into the receiving hole 9.

Figure 4A:
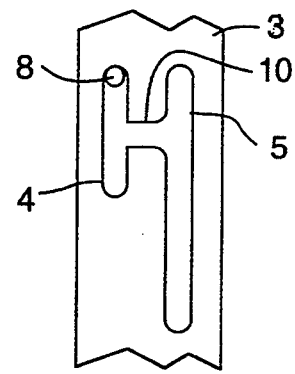
FIGS. 4A, 4B, and 4C illustrate the locking mechanism of the ophthalmic lance.
Figure 4B:
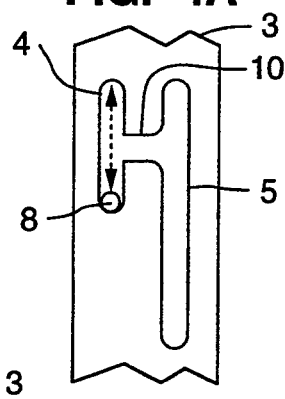
Figure 4C:
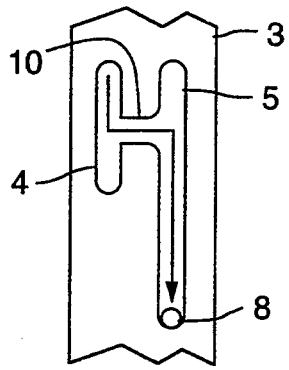

The function of the locking mechanism including the H-shaped cutout and the locking pin 8 is illustrated in FIGS. 4A, 4B, and 4C. To lock the ophthalmic lance so that the blade 7 cannot be exposed, the user must turn the sheath 3 in relation to the stem 2 so that the locking pin 8 is inside the short-leg 4 of the H-shaped cutout. When the locking pin 8 is in this position the stem 2 cannot be pushed down and the blade cannot be exposed.

To unlock the ophthalmic lance so that the blade 7 can be used, the user must turn the sheath 3 in relation to the stem 2 so that the locking pin 8 slides from the short-leg 4 of the H-shaped cutout through the cross-bar 10 and into the long-leg 5 of the H-shaped cutout as is illustrated in FIG. 4C. When the locking pin 8 is in this position the button on the stem 2 can be depressed so that the blade 7 is exposed. When the button 1 is released, the spring 6 causes the stem 2 to be pushed upward, thus retracting the blade 7 inside the sheath 3.

The locking pin 8 can also extend out of the H-shaped cutout so that the user can put pressure directly on the locking pin and cause the blade 7 to be exposed. This allows the user to operate the ophthalmic lance with one hand whereas when applying pressure on the button 1 the user must operate the ophthalmic lance with two hands. Releasing pressure on the locking pin 8 will cause the blade 7 to retract into the sheath 3.

Figure 4D:
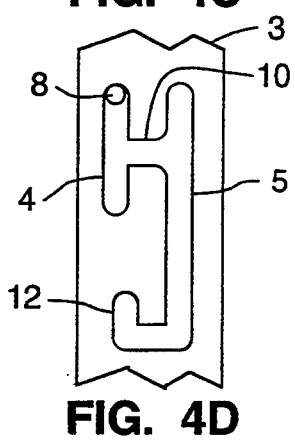
FIG. 4D illustrates an alternate locking mechanism for locking the blade of the ophthalmic lance in an exposed position.

In an alternate embodiment of the present invention, the alternate H-shaped cutout as shown in FIG. 4D is used so that the blade 7 can be locked in the exposed position. To lock the blade 7 in the exposed position the locking pin 8 is slid down the long-leg 5 and into the extension 12 so that the pin rests against the top of the extension 12 with pressure applied by the spring 6. This allows the user to lock the blade 7 in the exposed position. To put the blade 7 back inside the sheath 3, the stem 2 must be pushed down until the locking pin is at the bottom of the extension 12 and then rotated over so that the locking pin 8 is inside the long-leg 5 of the H-shaped cutout.

It will be apparent to one of reasonable skill in the art that various modifications may be made to the preferred embodiment without departing from the spirit and scope of the invention as defined by the appended claims.

I claim:

1. An ophthalmic lance for making incisions in a patient comprising:
  a. a blade including a stem;
  b. a hollow elongated sheath for slidably accepting the blade within a hollow interior wherein the blade has a limited travel range within the sheath from a first position wherein the blade is covered for protecting a user to a second position wherein the blade is exposed for making the incisions in a patient, the sheath having an H-shaped cutout through a wall of the sheath from the interior to an exterior, wherein pressure applied to a distal end of the blade propels the blade to the second position;
  c. a spring mounted inside of the sheath and resting against a stop means, the spring for automatically predisposing the blade into the first position when the pressure is released from the stem; and
  d. a locking pin for locking the blade in the first position so that it cannot be exposed when pressure is put on the stem, the locking pin slidably positioned inside of the H-shaped cutout and coupled to the stem, the locking pin positioned in a short leg of the H-shaped cutout when the blade is in the first position.

2. The ophthalmic lance as claimed in claim 1 wherein the H-shaped cutout is comprised of a short-leg, a long-leg and a cross-bar such that when the locking pin is slidably positioned inside of the short-leg, the blade is locked in the first position and when the locking pin is slidably positioned inside of the long-leg, pressure can be applied to the stem and the blade exposed, the locking pin slidably travelling from the short-leg to the long-leg through the cross-bar by rotation of the stem relative to the sheath.

3. A surgical instrument for making incisions in a patient comprising:
  a. a blade for making the incisions in the patient;
  b. a sheath slidably coupled to the blade by a stem and a locking pin, the sheath having a first position for covering the blade and a second position for exposing the blade, wherein the sheath is predisposed for automatically assuming the first position by a spring positioned inside of the sheath for pushing the stem upward; and
  c. an H-shaped cutout in the sheath for guiding positioning of the locking pin, having a long-leg and a short-leg with a cross bar in between, the short-leg for locking the blade in the first position when the locking pin is positioned in the short-leg and the long-leg for positioning the sheath in the second position when the locking pin is positioned in the long-leg and pressure is applied to the stem relative to the sheath.

4. A surgical instrument for making incisions in a patient comprising:
   a. a blade for making incisions in the patient;
   b. a hollow sheath slidably coupled to the blade for covering the blade;
   c. a stem coupled to the blade, the stem and the blade fitting inside of the sheath so that pressure applied to the stem exposes the blade;
   d. a spring for automatically retracting the blade inside the sheath when pressure is removed from the stem.;
   e. an H-shaped cutout, positioned through a wall of the hollow sheath having a short-leg, a long-leg and a cross-bar; and
   f. a locking pin coupled to the stem and slidably extending through the H-shaped cutout, so that when the locking pin is positioned to pass through the short-leg, the blade is spring-urged to a locked position inside of the sheath and when the locking pin is positioned to pass through the long-leg, pressure applied to the stem exposes the blade, the locking pin slidably travelling from the short-leg to the long-leg through the cross-bar by rotation of the stem relative to the sheath.

5. A surgical instrument for making incisions in patient comprising:
   a. a blade for making incisions in a patient;
   b. a stem coupled to the blade;
   c. a sheath slidably coupled to the blade and to the stem by a locking pin, the sheath having a first position for covering the blade and a second position for exposing the blade, wherein the sheath is predisposed for automatically assuming the first position;
   d. means for locking the sheath in the first position so that neither longitudinal pressure nor rotational pressure alone applied to the stem can expose the blade the means for locking comprised of an H-shaped cutout in the sheath for guiding positioning of the locking pin, having long-leg, a short-leg and a cross-bar, for locking the blade in the first position when the locking pin is positioned in the short-leg; and
   e. a spring which fits inside of the sheath and pushes the stem upward to predispose the sheath in the first position;
   wherein the blade is exposed by moving the sheath a portion of the distance between the first position and the second position and then applying an appropriate rotational pressure.

6. The surgical instrument as claimed in claim 5 wherein the blade is exposed by applying longitudinal pressure to the stem to position the locking pin adjacent the cross-bar and then applying an appropriate rotational pressure to slide the locking pin through the cross-bar.

7. The surgical instrument as claimed in claim 6 wherein the sheath is positioned in the second position when the locking pin is positioned in the long-leg and pressure is applied to the stem relative to the sheath.

8. The surgical instrument as claimed in claim 6 wherein the sheath is positioned in the second position when the locking pin is positioned in the long-leg and pressure is applied to the locking pin.

9. The surgical instrument as claimed in claim 6 wherein the sheath is positioned in the second position when the locking pin is positioned in the long-leg and pressure is applied to the stem or the locking pin.

10. The surgical instrument as claimed in claim 9 further comprising means for locking the blade in the first position.

* * * * *